United States Patent [19]

Pollack et al.

[11] Patent Number: 4,639,465
[45] Date of Patent: Jan. 27, 1987

[54] METHOD AND COMPOSITION FOR RELIEVING PAIN

[75] Inventors: Robert L. Pollack, Philadelphia; Lawrence Durst, Bridgeport, both of Pa.

[73] Assignee: Commonwealth Medical Corporation of America, Allentown, Pa.

[21] Appl. No.: 771,325

[22] Filed: Aug. 30, 1985

[51] Int. Cl.$^4$ .................. A61K 31/40; A61K 31/70; A61K 31/435

[52] U.S. Cl. .................. 514/419; 514/277; 514/23

[58] Field of Search .................. 514/419, 277, 23

[56] References Cited

U.S. PATENT DOCUMENTS

| | | | |
|---|---|---|---|
| 3,698,912 | 10/1972 | Winitz | 99/14 |
| 3,894,148 | 7/1975 | Ecker | 424/180 |
| 4,024,250 | 5/1977 | Palm | 424/180 |
| 4,085,207 | 4/1978 | Aoki et al. | 424/180 |
| 4,210,637 | 7/1980 | Wurtman et al. | 424/180 |
| 4,434,160 | 2/1984 | Jeretin et al. | 424/180 |
| 4,472,387 | 9/1984 | Laruelle et al. | 424/180 |
| 4,482,567 | 11/1984 | Tamir et al. | 424/274 |
| 4,530,790 | 7/1985 | Monoghan et al. | 260/239.3 P |
| 4,551,471 | 11/1985 | De Luca et al. | 514/419 |

OTHER PUBLICATIONS

"The Control of Brain Tryptophan Concentration", G. Curzon, Acta Vitamin Enzymol. (Milano), pp. 69-71, 1975.
The Effect of Sodium Salicylate on the Binding of L-Tryptophan to Serum Proteins, McArthur et al., *J. Pharm. Pharmac.*, 1969, pp. 744-750.
The Effect of Tryptophan on Postoperative Endodontic Pain, Shpeen et al., Oral Surgery, Oral Medicine and Oral Pathology, vol. 58, pp. 446-449, 1984.
Effects of Acetylsalicylic Acid on Serum Protein Binding and Metabolism of Tryptophan in Man, Smith et al., J. Pharm. Pharmac., vol. 23, pp. 180-189, 1971.
Brain Serotonin Turnover; Dependence on Free Tryptophan Concentration in Piasma, Gessa et al., Fedn. Proc. Fedn. Am. Soc., Exp. Biol. vol. 31, p. 2168, 1972.
Increase of Brain Tryptophan and Stimulation of Serotonin Synthesis by Salicylate, Tagliamonte et al., Journal of Neurochemistry, vol. 20, p. 909, 1973.
Influence of Plasma Tryptophan on Brain 5HT Synthesis and Serotonergic Activity, G. Curzon, Advances in Exptl. Med. Biol., vol. 133, pp. 207-219, 1981.
The Specific Binding of L-Tryptophan to Serum Albumin, McMenamy et al., J. Biol. Chem., vol. 233, No. 6, pp. 1436-1447, 1985.
Relationship Between Tryptophan Metabolism and Vitamin B$_6$ and Nicotinamide in Aged Subjects, Crepaldi et al., Acta Vitamin, Enzymol. (Milano), vol. 29, pp. 140-144, 1975.
High Doses of Vitamin B$_6$ in the Rat are Associated with Inhibition of Hepatic Tryptophan-Metabolism and Increased Uptake of Tryptophan into the Brain, Bender et al., Journal of Neurochemistry, vol. 43, No. 3, pp. 733-736.
5-Hydroxytryptamine and Pain Modulation in Man: A Clinical Pharmacological Approach with Tryptophan and Parachlorophenilalanine, Sicuteri et al., Acta Vitamin. Enzymol. (Milano), vol. 29, pp. 66-68, 1975.
Tryptophan in the Treatment of Depression, Young et al., Adv. Exptl. Med. Biol., vol. 133, pp. 727-737, 1981.
Pain II: New Approaches to Management, Fields, Annals of Neurology, vol. 9, No. 2, pp. 101-106, 1981.
The Nutritional Treatment of Pain, Warfield et al., *Hospital Practice*, pp. 100N-100P, 1983.
How Foods Affect the Way You Feel, *Good Housekeeping*, "The Better Way", p. 222, 1984.
The Effects of Dietary Tryptophan on Chronic Maxillofacial Pain and Experimental Pain Tolerance, Seltzer et al., J. Psychiat. Res., vol. 17, No. 2, pp. 181-186, 1982/83.
The Effects of Dietary Tryptophan on Chronic Maxillofacial Pain Tolerance, Seltzer et al., *Progress in Tryptophan and Serotonin Research*, pp. 325-330, 1984.
Tryptophan Availability and the Control of 5-Hydroxytryptamine and Tryptamine Synthesis in Human CNS, Young et al., Adv. Exptl. Med. Biol., vol. 133, pp. 221-230, 1981.
Chem. Abst. 97-197259y (1982), 100-33619v (1984).
"The Effects of Dietary Tryptophan on Chronic Maxillofacial Pain Tolerance", *Progress in Tryptophan and Serotonin Research*, 1984, pp. 325-330.
"The Effects of Dietary Tryptophan on Chronic Maxillofacial Pain and Experimental Pain Tolerance", *J. Psychiac. Res.*, vol. 17, No. 2, pp. 181-186, 1982/83.

*Primary Examiner*—Stanley J. Friedman
*Attorney, Agent, or Firm*—Lawrence J. Shurupoff

[57] ABSTRACT

Intractable chronic pain is eliminated or relieved through administration of a composition including L-tryptophan in combination with fructose, pyridoxine and niacinamide. Each ingredient either promotes the transport of L-tryptophan from the blood plasma across the blood-brain barrier into the brain or promotes the conversion of L-tryptophan within the brain to the neurotransmitter serotonin.

10 Claims, No Drawings

METHOD AND COMPOSITION FOR RELIEVING PAIN

BACKGROUND OF THE INVENTION

1. Field of the Invention

This invention relates generally to a dietary supplement for decreasing or eliminating pain and particularly relates to a composition which promotes the transport of tryptophan from the blood into the brain.

2. Description of Prior Developments

Attention has recently turned to nontraditional methods and compositions for reducing pain in an effort to provide relief in those instances where standard techniques have proven ineffective and where it is desired to avoid the well-known drawbacks of conventional analgesics. One approach has been to attempt to relieve pain through dietary supplementation of L-tryptophan (tryptophan). Once within the brain, neurons convert tryptophan into the neurotransmitter serotonin. It has been found that an increase of tryptophan in the brain increases the brain production of serotonin which has been shown to be linked to sleep, appetite, depression, and pain threshold. Disturbances in the brain causing reduced levels of serotonin have been linked to clinical depression, insomnia, and lowered pain threshold. The latter abnormality results in chronic intractable pain.

It is known that dietary supplementation of tryptophan increases the blood level of tryptophan and facilitates the passage of tryptophan across the blood-barrier into the brain. The increased amount of tryptophan in the brain permits a greater amount of tryptophan to be converted to the compound, serotonin.

The level of one's pain threshold, a mechanism that normally prevents the brain from interpreting stimuli below a certain level as pain, is directly related to the amount of serotonin that is present in the brain. The higher the level of serotonin that is present, the higher will be the pain threshold level, up to a normal maximum level. With normal amounts of serotonin one can function in a normal manner and not be subjected to myriad numbers of stimuli such as from muscle activity, that could manifest themselves as pain impulses.

In order for tryptophan to be converted to serotonin in the brain, it must cross a separating mechanism that exists between the blood vessel and the brain. To reach the brain, tryptophan requires a carrier transport mechanism which, literally, carries tryptophan across this very selective blood-brain barrier and into the brain. Because of its polar nature, tryptophan requires a carrier protein to transport it across the blood-brain barrier. Not only is tryptophan carried by this transport mechanism, but other selected amino acids, called large neutral amino acids, (LNAAs) are carried as well. Tryptophan not only has to compete with these LNAAs for access to the transport carrier mechanism, it also has a lower affinity for the carrier system than does the LNAAs. To compound this situation further, tryptophan in foods is generally present in lower amounts than the LNAAs - particularly in animal proteins. All of these factors contribute to the amount of tryptophan that actually gets through to the brain, to be finally converted into serotonin.

There are numerous conditions, improper diet constitutes one of them, that can interfere with, and decrease, the amount of tryptophan that normally passes through the blood-brain barrier into the brain each day. This comes about when the ratio of tryptophan to LNAAs in the blood going to the brain is lower than normal. This means that the number of molecules of tryptophan present at the blood-brain barrier is much smaller than the number of LNAAs present at the same blood-brain barrier. The LNAAs overwhelm the tryptophan and very little tryptophan is provided passage into the brain, compared to the number of LNAAs that are provided passage.

In the attempt to correct this improper tryptophan/LNAA ratio, it was found that increasing the total protein intake, obtained from normal dietary sources, in order to add more tryptophan to the system, results, paradoxically, in an even greater decrease in the pain threshold level. This is so because there are usually more LNAAs than there is tryptophan in food. Experimental studies have established the fact that increasing the amount of protein as food, in order to improve the tryptophan/LNAA ratio, only makes the tryptophan/LNAA ratio worse because of the greater intake of the LNAAs over the intake of the tryptophan.

With less tryptophan getting into the brain, less serotonin is formed, and the pain threshold is lowered. Whereas, under normal conditions, low-level sensory perceptions interpreted by the body as pain stimuli would have been filtered out by the normal pain threshold level, they are now experienced as pain. This pain can span the gamut from relatively insignificant annoyances to chronic, unremitting, intractable, excrutiating pain. Because this type of pain stems from a biochemical imbalance involving the tryptophan-serotonin relationship which cannot be corrected by any medication, it is unmanageable by any conventional drug therapy - because the drug does not address itself to the correction of this specific biochemical imbalance.

Accordingly, a need exists for a method and composition for transporting an effective dose of tryptophan across the blood-brain barrier into the brain and for promoting the conversion of tryptophan into serotonin.

SUMMARY OF THE INVENTION

The present invention has been designed to provide the proper dietary supplementation of trytophan which will decrease or eliminate chronic pain, particularly in those conditions where the pain stems from an unknown origin, and not due to any known medical, dental or psychological reason.

The administration of pure tryptophan will: (1) help to improve the ratio of blood tryptophan to blood LNAAs, (2) help to increase the amount of tryptophan that will enter the brain, and (3) help to increase the serotonin level and raise the pain threshold level.

The oral administration of tryptophan under proper dietary conditions thus provides a supplementary intake of this particular amino acid which helps to correct an improper tryptophan/LNAA ratio. The dietary supplementation of tryptophan, combined with an adjusted protein, low fat, higher carbohydrate intake, results in a significant reduction in the pain intensity experienced by chronic pain patients.

A particularly effective composition has been found to include tryptophan, niacinamide, pyridoxine, and a carbohydrate such as a sugar. A most effective sugar has been found to be fructose, which yields a steadily metered release of insulin into the blood. This evenly controlled release of insulin is required for optimally practicing the invention.

It is therefore an object of the invention to provide a method and composition for relieving pain through dietary supplementation of tryptophan.

Another object is to effeciently transport tryptophan across the blood-brain barrier so that an effective pain relieving quantity of tryptophan is converted in the brain to serotonin.

Still another object of the invention is to provide a method and composition for promoting the conversion of tryptophan to serotonin within the brain.

Yet another object is to provide a method and composition for relieving pain which triggers the release of insulin at an even rate in order to augment the steady transport of tryptophan across the blood-brain barrier.

Various other objects, features and attendant advantages of the present invention will be more fully appreciated as the same becomes better understood from the following detailed description.

DETAILED DESCRIPTION OF THE PREFERRED EMBODIMENTS

As briefly stated above, there are four operative ingredients which, when combined according to the invention, yield an effective composition for promoting the transport of tryptophan from the blood plasma into the brain. Once in the brain, tryptophan is converted to serotonin which has been shown to increase one's pain threshold level. In addition to the primary ingredient tryptophan, three additional ingredients are provided to facilitate tryptophan transport into the brain and/or to promote its conversion into serotonin.

Niacinamide is the first additional ingredient which promotes or facilitates tryptophan transport into the brain. Niacin is an essential nutrient that the human body must have at all times. Because of niacin's importance, the body has evolved a method by which it can synthesize niacin from tryptophan. More particularly, 60 milligrams of tryptophan is used by the body to make each milligram of niacin. Studies in humans have shown that the amount of niacin the body gets from tryptophan amounts to about one-half of the total amount of niacin that the body needs each day, that is, about 13-19 mg. This means that from $(13/2 \times 60)$ mg to $(19/2 \times 60)$ mg or 390 mg to 570 mg of tryptophan is needed each day for its conversion to niacin.

In order to attempt to minimize the destruction of the supplemental tryptophan within the body via synthesis into niacin, niacinamide or nicotinamide is included along with the tryptophan to provide the body with the pre-formed vitamin niacin.

The next operative ingredient of the invention is pyridoxine (vitamin $B_6$). Pyridoxine is essential in the tryptophan-serotonin conversion process and is part of the enzyme system which functions directly in the conversion of tryptophan to serotonin. By providing the body with this vitamin at the same time that the supplemental tryptophan is administered, this important nutrient will be provided to individuals whose dietary intake may have been deficient. This will ensure efficient conversion of tryptophan to serotonin.

The last ingredient, but possibly the most important, is the monosaccharide sugar, fructose. Investigations have shown that dietary carbohydrate causes an increase in the relative concentration of blood tryptophan levels; i.e., the amount of tryptophan is increased relative to the amount of the interfering large neutral amino acids that compete with tryptophan for the transport carrier mechanism in the brain. Of all the blood amino acids, tryptophan is the only amino acid that is carried as an albumin-bound complex. All of the other amino acids, including the LNAAs, travel in the blood as the free amino acids.

Insulin, when elaborated into the blood stream in response to an increase in blood sugar concentration serves to drive amino acids into the body tissues while the blood courses on its way to the brain. The tryptophan-albumin complex is not affected by this insulin action, and thus remains available to reach the brain. Thus, this complex is not "lost" to the body tissues. However, the other amino acids are removed from the blood thereby increasing the relative percentage of tryptophan in the blood. Carbohydrate intake, therefore, with its insulin-releasing action, helps to improve the tryptophan/LNAA ratio in favor of the tryptophan and increases the amount of tryptophan crossing the blood-brain barrier into the brain.

Fructose is included in each capsule as a preferred source of carbohydrate to achieve this insulin/LNAA/tryptophan effect. While the weight percentages of each ingredient listed below could vary up to approximately 50%, a preferred composition of the invention for an effective single (capsule) dosage for a typical patient is as follows:

1. L-tryptophan (one of the eight essential amino acids found in most protein foods) . . . 250 mg (45.5% by weight)
2. Niacinamide (Niacin or nicotinamide, a natural vitamin found in such foods as meat, whole grains, poultry and fish) . . . 25 mg (4.5% by weight)
3. Pyridoxine (Vitamin $B_6$, a natural vitamin found in such foods as meat, whole grains, poultry and fish) . . . 25 mg (4.5% by weight)
4. Fructose (a natural sugar found in such foods as fruits and honey) . . . 250 mg (45.5% by weight)

The effective single dosage listed above as expressed in parts by weight would be 5 to 15 parts by weight of L-tryptophan, ½ to 3/2 parts by weight of niacinamide, ½ to 3/2 parts by weight of pyridoxine, and 5 to 15 parts by weight of fructose.

Because the above composition can be taken orally in amounts up to 10-12 capsules daily, the inclusion of the sugar, fructose, was deliberately selected rather than glucose or sucrose because of studies which indicated that the response of the body in releasing insulin into the blood was much more even with fructose than was shown for the other sugars that were used and without any sudden insulin upsurge. Thus, fructose provides the desired predictability of insulin release needed for a constant production of serotonin which in turn is required for the satisfactory even relief of pain.

Obviously, numerous modifications and variations of the present invention are possible in light of the above teachings. It is therefore to be understood that within the scope of the appended claims, the invention may be practiced otherwise than as specifically described herein. For example, other carbohydrates could be used in place of fructose without departing from the spirit of the invention.

What is claimed is:

1. A dietary supplement for increasing a patient's threshold of pain via steady and prolonged production of serotonin withinthe patient's brain, comprising:
approximately 5 to 15 parts by weight of L-tryptophan for increasing said production of serotonin and approximately 5 to 15 parts by weight of fructose for producing a steady release of insulin into the patient's blood increasing transport of L-tryptophan from the patient's blood plasma into the patient's brain.

2. The dietary supplement of claim 1, further comprising approximately ½ to 3/2 parts by weight of a niacin supplement selected from the group consisting of niacin and nicotinamide.

3. The dietary supplement of claim 1, further comprising approximately ½ to 3/2 parts by weight of pyridoxine for promoting the conversion of tryptophan into serotonin within the patient's brain.

4. The dietary supplement of claim 1, further comprising approximately ½ to 3/2 parts by weight of pyridoxine and approximately ½ to 3/2 parts by weight of a niacin supplement selected from the group consisting of niacin and nicotinamide.

5. A method for increasing a patient's threshold of pain via steady and prolonged production of serotonin within the patient's brain, comprising:
administering to the patient an effective dosage of L-tryptophan for increasing production of serotonin within the patient's brain and an effective dosage of fructose for producing a steady release of insulin into the patient's blood for increasing transport of L-tryptophan from the patient's blood plasma into the patient's brain.

6. The method of claim 5, which further comprises administering to the patient an effective dosage of a niacin supplement selected from the group consisting of niacin and nicotinamide.

7. The method of claim 5, which further comprises administering to the patient an effective dosage of pyridoxine for promoting the conversion of tryptophan into serotonin within the patient's brain.

8. The method of claim 5, which further comprises administering to the patient an effective dosage of pyridoxine and an effective dosage of a niacin supplement selected from the group consisting of niacin and nicotinamide.

9. The methods of claim 5, which further comprises administering to the patient said dosages of L-tryptophan and fructose at predetermined intervals up to twelve times daily.

10. The method of claim 9, wherein said dosage of L-tryptophan comprises a 250 mg dosage and said dosage of fructose comprises a 250 mg dosage.

* * * * *